United States Patent [19]
Hartmann, Jr.

[11] 4,319,490
[45] Mar. 16, 1982

[54] MULTIPLE WEDGE ELEMENT LENS FOR AN ULTRASONIC INSPECTION TRANSDUCER

[75] Inventor: Henry Hartmann, Jr., Passaic County, N.J.

[73] Assignee: The United States of America as represented by the Secretary of the Army, Washington, D.C.

[21] Appl. No.: 126,804

[22] Filed: Mar. 3, 1980

[51] Int. Cl.³ ............................................. G01N 29/00
[52] U.S. Cl. ...................................... 73/642; 310/335
[58] Field of Search ................. 73/642, 644; 367/150; 181/176; 310/335

[56] References Cited

U.S. PATENT DOCUMENTS

| | | | |
|---|---|---|---|
| 3,283,264 | 11/1966 | Papadakis | 310/335 |
| 3,924,453 | 12/1975 | Clark et al. | 73/642 |
| 4,044,273 | 8/1977 | Kanda et al. | 367/150 |
| 4,084,582 | 4/1978 | Nigam | 73/642 |

Primary Examiner—Stephen A. Kreitman
Attorney, Agent, or Firm—Nathan Edelberg; Robert P. Gibson; A. Victor Erkkila

[57] ABSTRACT

A plurality of flat or curved, wedge-shaped elements form the surface of a lens of an ultrasonic inspection transducer. The multiple wedge-shaped elements permit the ultrasonic energy from the transducer to be focused (1) in a substantially straight line (line focus) parallel to the axis of the lens and (2) deflected from a plane parallel to the wedge-shaped elements and at an oblique angle to the line focus. This achieves a concentration of ultrasonic energy along a line that can be projected into material as shear waves while maintaining equidistance from the transducer's sensing wafer. This results in a concentration of ultrasonic energy that can detect small cracks in a workpiece. Further, with this lens, wider ultrasonic scan may be made with minimal errors in detection. This lens also provides accurate location information on depth of flaws. Furthermore, the novel lens is the only known shape that can achieve reduced errors, wide transducer scan, accurate depth location information and small crack detection of circumferential cracks in tubular shaped products as well as cracks oriented parallel to the direction of scan in flat plates. The same concept can be used on a flat lens (rather than curved cylindrical) with straight multiple wedge elements to minimize errors of flaw detection and identification of flaw location in flat and tubular workpieces while maintaining a wide path of scan.

12 Claims, 8 Drawing Figures

U.S. Patent  Mar. 16, 1982  4,319,490

MULTIPLE WEDGE ELEMENT LENS FOR AN ULTRASONIC INSPECTION TRANSDUCER

GOVERNMENT RIGHTS

The invention described herein may be manufactured and/or used by or for the Government for governmental purposes without the payment of any royalty thereon.

BACKGROUND OF THE INVENTION

The invention relates generally to nondestructive ultrasonic pulse-echo inspection of workpieces, and particularly to an improved lens for directing the ultrasonic energy into a workpiece.

The nondestructive ultrasonic inspection of a workpiece is a well-developed technique. Briefly, in a typical inspection set-up for flat or curved plate, the workpiece to be inspected and a source of ultrasonic energy (usually a transducer and lens), are placed in close proximity to one another and may be joined by a coupling fluid such as water. Energy from the lens is directed from a sensing wafer through the lens toward the workpiece, refracted at the workpiece surface from longitudinal into shear mode and reflected inside the workpiece back to the sensing wafer. Variations in reflected energy received by the sensor indicate presence of a crack or flaw in the workpiece.

Heretofore in a typical ultrasonic inspection apparatus, a flat lens directs ultrasonic energy through a coupling medium, e.g. water into the workpiece. Either the transducer or the workpiece moves so that the width of ultrasonic energy sweeps through the workpiece. Often, shear waves are used to detect cracks. Shear waves are created inside the workpiece by tilting the transducer relative to the surface of the workpiece. Ideally, the ultrasonic energy should be concentrated in a straight line parallel to the surface of the workpiece. However, the tilt inclines the focal zone (far field) of energy so that it is not parallel to the surface. This is undesirable in that it limits the width of the scan path and prevents uniform accuracy of flaw detection over the width of the scan path.

In the present invention, there is a novel cylindrical or flat lens having curved or straight multiple wedge-shaped elements that focus the ultrasonic energy in a shear mode substantially in a straight line parallel to the surface within a workpiece. The advantages of this arrangement are (1) errors in detection are minimized by maintaining a constant measurement accuracy over the entire width of the scan; (2) wide transducers can be used to generate wide paths of scan; (3) flaws can be accurately located as to depth within the workpiece; and (4) the lens of the present invention is the only known shape of lens that can achieve the above three advantages on circumferential cracks in tubular shaped products as well as on cracks oriented parallel to scan movement in flat shaped workpieces.

SUMMARY OF THE INVENTION

According to one aspect of the invention there is provided an improved lens for an ultrasonic transducer. The face of the lens has a plurality of wedge-shaped elements, each inclined at an angle from the axis of the overall lens. The elements are of uniform width, and angle of inclination.

DETAILED DESCRIPTION OF THE DETAILED EMBODIMENT

Figure 1:
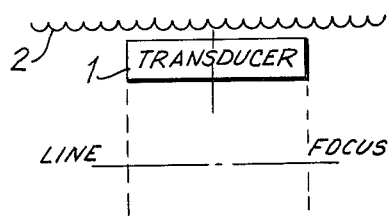
FIGS. 1 and 2 are respectively schematic front and side views of an ultrasonic transducer and lens in a coupling media illustrating certain principles involved in ultrasonic testing.
Figure 2:
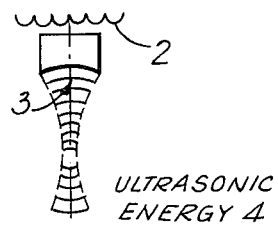

Referring now to FIGS. 1 and 2, there is shown a front and side view of a prior art transducer 1 with a cylindrical lens 3 immersed in a coupling fluid, the surface of which is shown by the waveline 2. In these FIGS. and the subsequent ones, the mounting for the transducer with lens and piezocrystal "active elements" are not shown. As shown in FIG. 2, the bottom side of the lens from which the ultrasonic energy emerges, has a cylindrical surface. This curved surface focuses the ultrasonic energy close to a line focus. In other words, the ultrasonic energy concentrates in a zone about the line focus. In this arrangement, the line focus is always at right angles to the flow of ultrasonic energy. It is desirable to have an intense concentration of ultrasonic energy within a workpiece being inspected in order to detect smaller cracks. Also, a uniform distribution of the energy along the scan will minimize errors.

Figure 3:
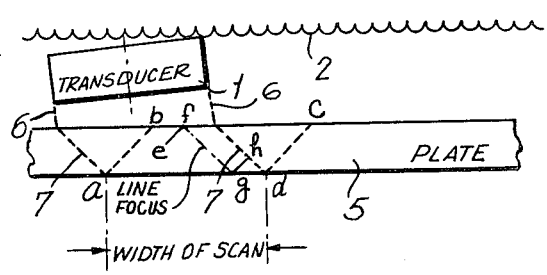
FIG. 3 is a schematic front sectional view of a prior art ultrasonic transducer and lens, and flat workpiece illustrating certain aspect of the prior art.

FIG. 3 is a schematic sectional front view, illustrating the prior art transducer with cylindrical lens 3, in a coupling medium whose surface is shown by legend 2, and in position for inspecting a plate 5. The plate 5 is shown in cross section and extends perpendicular to the sheet of the drawing. The transducer and plate move relative to one another in the plane perpendicular to the sheet of the drawing, and inspection is done over the path defined by this movement and the width of scan of the ultrasonic beam. In the FIG. 3, dotted lines 6—6 indicate the width of the ultrasonic energy flowing from the transducer to the plate. Some of the ultrasonic energy, at the interface with the plate, is refracted and changed into shear energy as indicated by dotted lines 7—7 and then reflected off the bottom surface of the plate between points a and d. Some of the reflected energy returns to the transducer along the path just described. Much of the reflected ultrasonic energy continues on to the upper surface of the plate between b and c where a portion is again reflected back along the path just described to the transducer.

The transducer 1 is tilted approximately 10 degrees with respect to the plate being inspected in order to refract more sensitive shear energy into the plate. Put another way, the axis of the cylindrical lens is not parallel with the plate. This causes the line focus of ultrasonic energy to be tilted at approximately a 45 degree angle to the plane or top surface of the plate and causes unequal dispersion of energy over the width of the scan. In FIG. 3, the region of scan within which cracks are to be detected in the plate is a, b, c, d. The line focus about which the ultrasonic energy is concentrated consists of three jointed continuous straight line segments e,f, f,g and g,h within the region of scan. The line focus segment e,f consists of a reduced intensity of energy, since approximately 80 percent of energy is lost in reflections off the bottom and top surfaces, respectively, of the plate. The central line focus segment f,g consists of approximately 45 percent of the intensity that it could have had if it had not reflected off the bottom surface of the plate. The line focus segment g,h remains at full intensity as it has not reflected off any surface of the plate. If a crack exists in the plate oriented normal to the plane of the sheet of the drawing, as the region of scan passes over it, an echo would be reflected from the position. The closer the crack happens to be to the line of focus, and the less reflection the line focus has experienced from the plate surfaces, the larger will be the reflected echo of the crack. If during scanning there is little overlap of the width of scan paths (note the plate of the transducer is moving perpendicular to the sheet of the drawing), an encountered crack may or may not be detected depending on how close it comes to the line focus and which portion of the line focus is approached within the region of scan. Obviously, this is a cause for error. It is desired that the line focus be parallel to the plate so that it can be in close proximity to all regions of the scan. This could be achieved with commercially available transducer and lenses before this invention.

Figure 4:
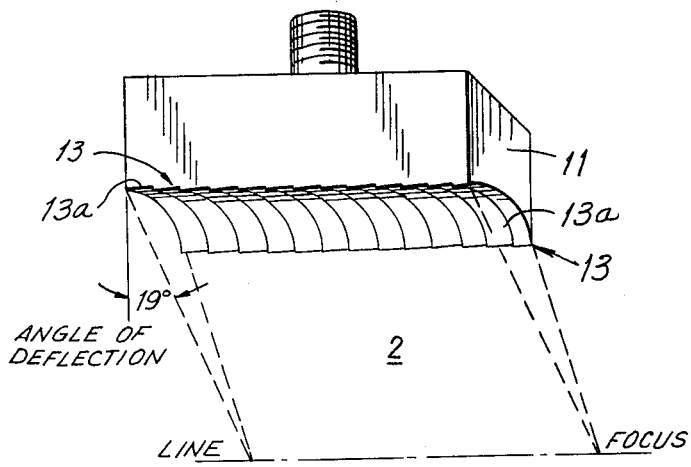
FIG. 4 is a perspective view looking up at the multiple wedge-shaped elements of the cylindrical lens of this invention.

FIG. 4 is a perspective view looking up at the cylindrical surface of an improved transducer lens made in accordance with the invention. A transducer is shown at 11, and its cylindrical lens surface 13 is composed of a series of wedge-shaped elements 13a. These elements 13a are all uniformly curved, and are inclined at the same angle. The angle of the wedge elements refracts ultrasonic energy as it emerges from the lens into the coupling medium 2. Shown is an angled path for example of 19°. In FIG. 4 there are shown thirteen such wedge-shaped elements 13a that make up the lower surface of the lens. The wedge-shaped elements concentrate the ultrasonic energy into a line focus which is essentially a straight line.

Figure 5:
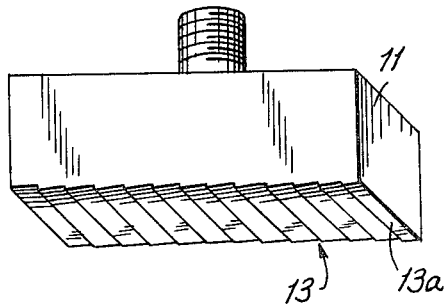
FIG. 5 is a perspective view looking up at the multiple wedge-shaped elements of a flat lens of this invention.

FIG. 5 illustrates the same concept of multiple element wedges applied to a flat lens.

Figure 6:
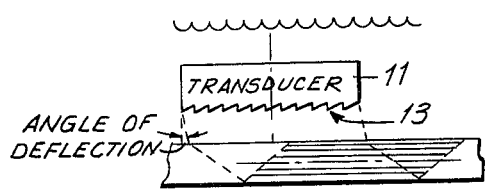
FIGS. 6 and 7 are respectively schematic front and side sectional views of the ultrasonic lens of the present invention, workpiece, and coupling medium illustrating certain aspects of the operation of the lens of the present invention.
Figure 7:
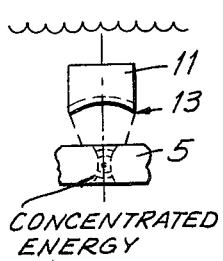

The result of using the wedge-shaped lens during inspection is illustrated in FIGS. 6 and 7. The transducer 11 and plate 5 are parallel to one another. With the multiple element wedge lens 13, the flow of ultrasonic energy is refracted at an angle from a line perpendicular to the focused line (line focus). When it enters the workpiece it is refracted again and converted into shear energy which at the proper angle is more sensitive to flaws. The line focus is parallel to the plate being tested. Thus the energy, concentrated uniformly along the line focus, is in a straight line parallel to the surfaces of the plate. This produces a number of important results. Since the energy is symmetrically distributed over the entire width of scan, the transducer may be made wider, and wider widths of scan can be used than with devices heretofore used. In other words, wide transducers can be used to generate wide paths of scan. Second, errors in detection are minimized because the ultrasonic energy is substantially uniformly distributed over the width of scan. For example, when the region of scan encounters a crack, no matter which portion of the scan the crack is located in, the same echo will be reflected. Third, the piezocrystal active element behind the lens is equidistant along the path of energy to the top surface of the workpiece. Therefore, a defect located anywhere within the workpiece will provide the same location of depth signal anywhere within the scan. A fourth advantage is that this is the only known shape that can achieve the first three advantages on detecting the presence of circumferential cracks in tubular shaped products and detecting cracks oriented in the general direction of the scan in flat plates.

Figure 8:
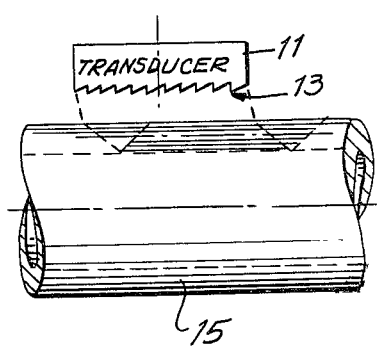
FIG. 8 is a front view, partially in sections, illustrating the lens of the invention and a tubular workpiece under test.

The last feature is illustrated in FIG. 8. In this FIG. the transducer 11 is shown with its multiple element wedge lens 13 positioned above the outer surface of a tube 15. The axis of the cylindrical lens is parallel to the axis of the tube 15. Thus the ultrasonic energy from the transducer is concentrated around the line focus and is parallel to those two axes. This permits the uniform distribution of ultrasonic shear energy within the region of scan. This is a desirable arrangement for the detection of circumferential cracks located within the walls of the tubing. This eliminates errors of detection and location that would previously occur without application of a curved multiple wedged element lens.

In a preferred embodiment of the present invention, a typical lens would have the following dimensions:
radius of the cylindrical lens: 20 M.M. to infinity
length of each element (length of lens arc in FIG. 7): 6 to 25 M.M.
width of transducer (horizontal dimension of transducer in FIG. 6): 6 to 100 M.M.
number of wedges per transducer width: 1 or more for every 2.5 M.M.
frequency of ultrasonic energy: 1 to 10 M.Hz.
material from which the lens is made: plastic.

I claim:

1. An improved lens for an ultrasonic transducer comprising a flat or cylindrically concave face including multiple wedge shaped elements superimposed on said face forming said lens, wherein said elements are each inclined at a uniform angle from said face so as to refract ultrasonic rays at a uniform angle from a line perpendicular to said face and in a parallel pattern in a plane which is normal both to said face and said wedge shaped elements.

2. A lens according to claim 1 wherein said elements are of uniform width,

3. A lens according to claim 2 wherein said angle of inclination is such that it induces sensitive shear waves into the workpiece.

4. A lens according to claim 2 wherein the width of an element is 2.5 or less MM.

5. A lens according to claim 4 having at least 10 wedge-shaped elements.

6. A lens according to claim 1, or 2, or 3, or 4, or 6 wherein said lens has a cylindrically concave face and the refracted rays are concentrated along a straight line focus parallel to the axis of said lens.

7. A lens according to claim 1, or 2, or 3, or 4, or 6 wherein said lens has a flat face.

8. In an ultrasonic testing apparatus in which a transducer has a lens for generating ultrasonic energy and a workpiece adapted to be positioned to receive said energy and for relative movement of the transducer and workpiece to be examined, the improvement comprising: The transducer lens being oriented parallel to the surface of the workpiece to be tested, said lens having a flat or cylindrically concave face comprising a plurality of wedge shaped elements superimposed on said face, each inclined at a uniform angle from said face so as to refract ultrasonic rays at a uniform angle from a line perpendicular to said face and in a parallel pattern in a plane which is normal both to said face and to said wedge shaped elements.

9. In an apparatus according to claim 8 wherein said lens has a cylindrically concave face and the refracted rays are concentrated along a straight line focus parallel to the axis of said lens.

10. In an apparatus according to claim 9 wherein said elements are of uniform width, radius, and angle of inclination.

11. In an apparatus according to claim 8 wherein said lens has a flat face.

12. In an apparatus according to claim 11 wherein said elements are of uniform width, and angle of inclination.

* * * * *